(12) United States Patent
Sutter

(10) Patent No.: US 6,227,859 B1
(45) Date of Patent: May 8, 2001

(54) DENTAL IMPLANT AND DEVICE WITH A DENTAL IMPLANT

(75) Inventor: Franz Sutter, Bennwilerstrasse 42, CH-4435 Niederdorf (CH)

(73) Assignee: Franz Sutter, Niederdorf (CH)

( * ) Notice: Subject to any disclaimer, the term of this patent is extended or adjusted under 35 U.S.C. 154(b) by 0 days.

(21) Appl. No.: 09/424,509

(22) PCT Filed: May 18, 1998

(86) PCT No.: PCT/EP98/02905

§ 371 Date: Mar. 8, 2000

§ 102(e) Date: Mar. 8, 2000

(87) PCT Pub. No.: WO98/52488

PCT Pub. Date: Nov. 26, 1998

(30) Foreign Application Priority Data

May 24, 1997 (CH) .................................................. 1219/97

(51) Int. Cl.[7] .................................................. A61C 8/00
(52) U.S. Cl. .................................................. 433/173
(58) Field of Search .................. 433/172, 173, 433/174

(56) References Cited

U.S. PATENT DOCUMENTS

| | | | |
|---|---|---|---|
| 4,960,381 | * | 10/1990 | Miznick ................................. 433/174 |
| 5,125,840 | * | 6/1992 | Dürr et al. ............................ 433/173 |
| 5,195,892 | * | 3/1993 | Gersberg ............................... 433/174 |
| 5,302,126 | * | 4/1994 | Wimmer et al. ...................... 433/173 |
| 5,312,253 | * | 5/1994 | Chalifoux ............................. 433/173 |
| 5,577,912 | * | 11/1996 | Prins ..................................... 433/172 |
| 5,667,384 | * | 9/1997 | Sutter et al. .......................... 433/172 |
| 5,695,335 | * | 12/1997 | Haas et al. ............................ 433/173 |
| 5,782,918 | * | 7/1998 | Klardie et al. ....................... 433/172 |
| 5,823,776 | * | 10/1998 | Duerr et al. .......................... 433/173 |

FOREIGN PATENT DOCUMENTS

| | | | |
|---|---|---|---|
| 41 27 839 | * | 3/1992 | (DE) . |
| 92 02 396 | * | 4/1992 | (DE) . |
| 195 34 979 | * | 1/1997 | (DE) . |
| 0 475 299 | * | 3/1992 | (EP) . |
| 0 685 208 | * | 12/1995 | (EP) . |
| 2 733 144 | * | 10/1996 | (FR) . |

* cited by examiner

Primary Examiner—Ralph A. Lewis
(74) Attorney, Agent, or Firm—Evenson, McKeown, Edwards & Lenahan, P.L.L.C.

(57) ABSTRACT

The invention relates to a dental implant which has an axis and a hole with a positioning section. Said positioning section has projecting parts and intermediate spaces distributed alternately, one after the other, along the periphery. Said intermediate spaces comprise several first intermediate spaces which create a division, and a second, wider intermediate space. A secondary and/or supplementary structural part can be attached in the implant, said part having a connecting section which extends into the hole. Said connecting section can have projecting parts for engaging in the intermediate spaces of the implant, and can be configured in such a way that it can be fixed to the implant in several different rotated positions or a single rotated position. The secondary and/or supplementary structural part can also be produced without projecting parts of the type mentioned, so that it can be screwed into the implant.

11 Claims, 10 Drawing Sheets

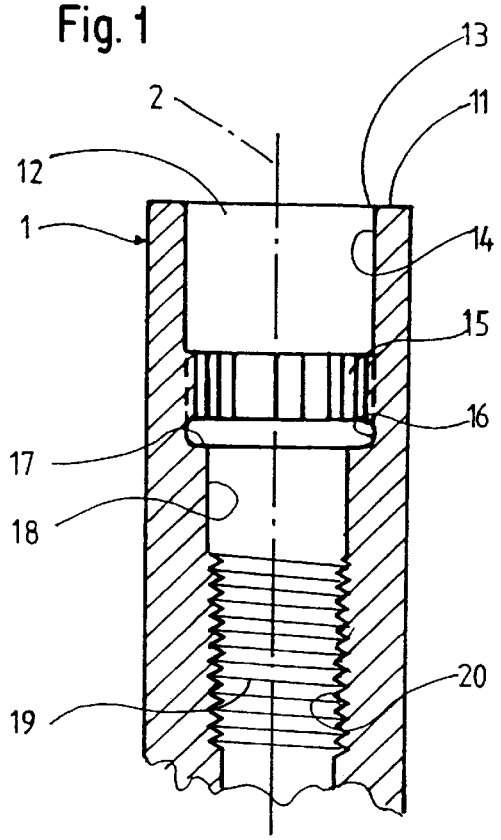
Fig. 1
Fig. 2
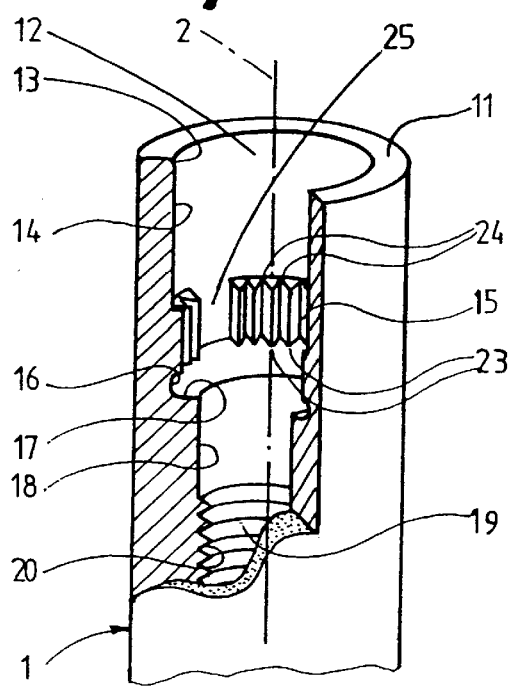
Fig. 3
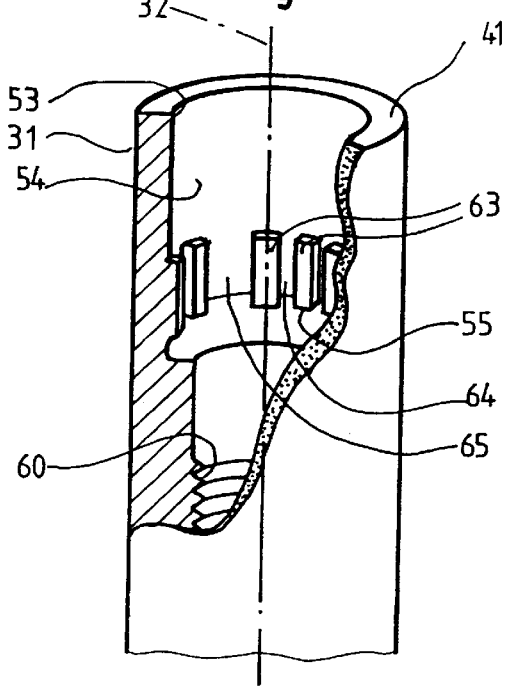
Fig. 4

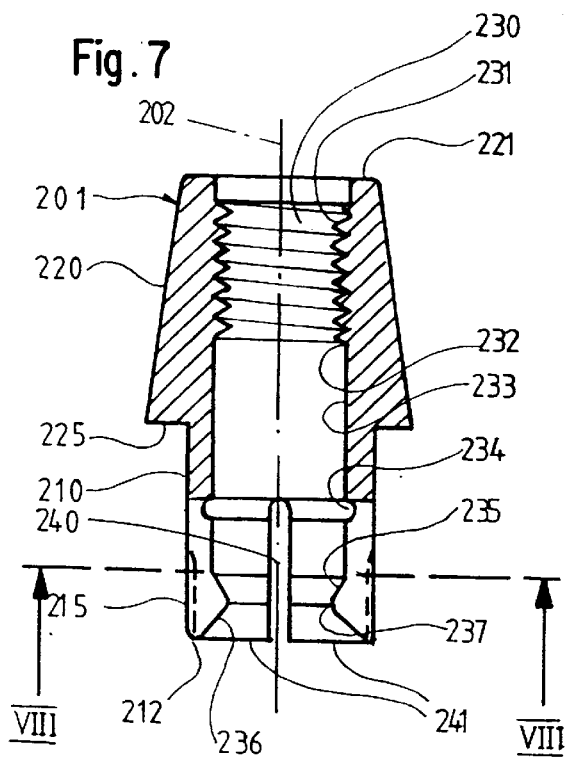
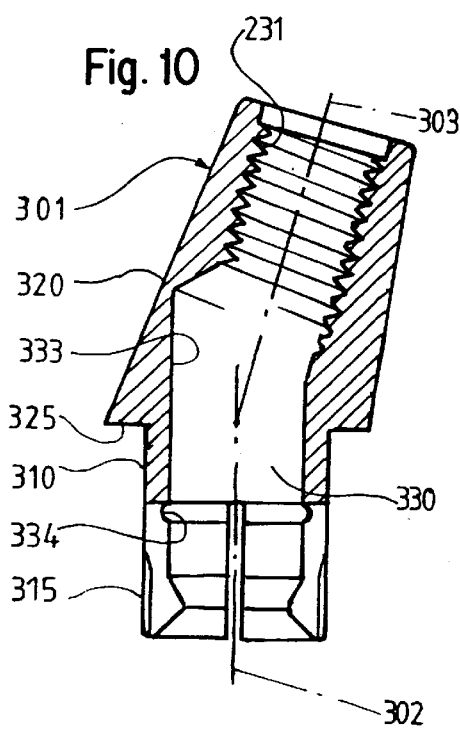
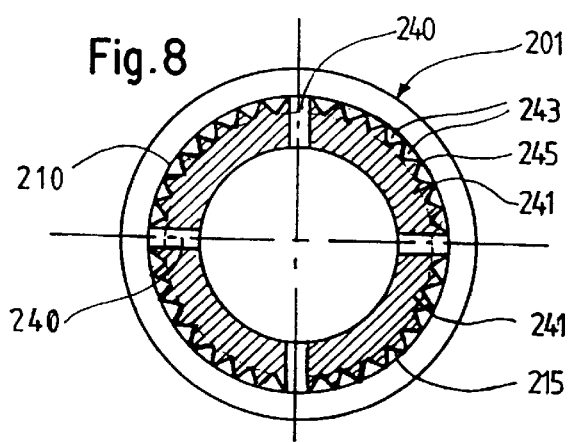
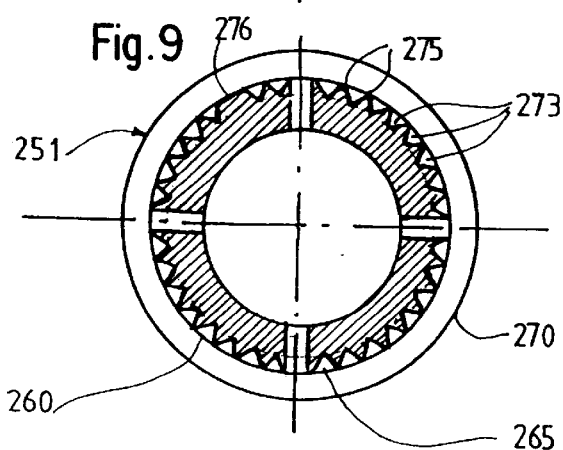
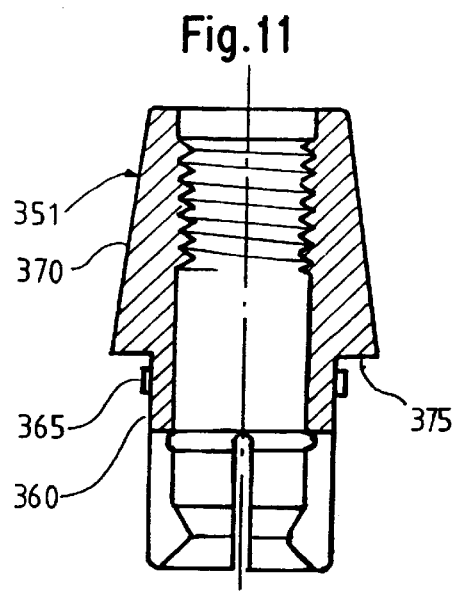

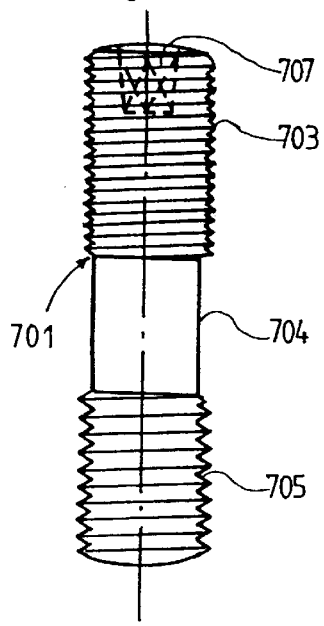
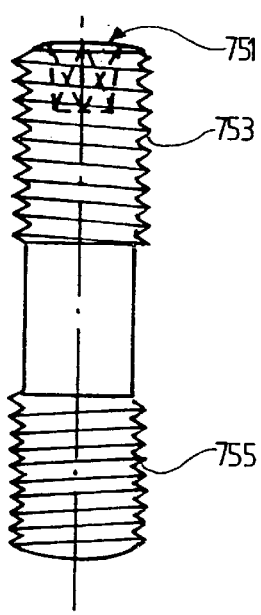
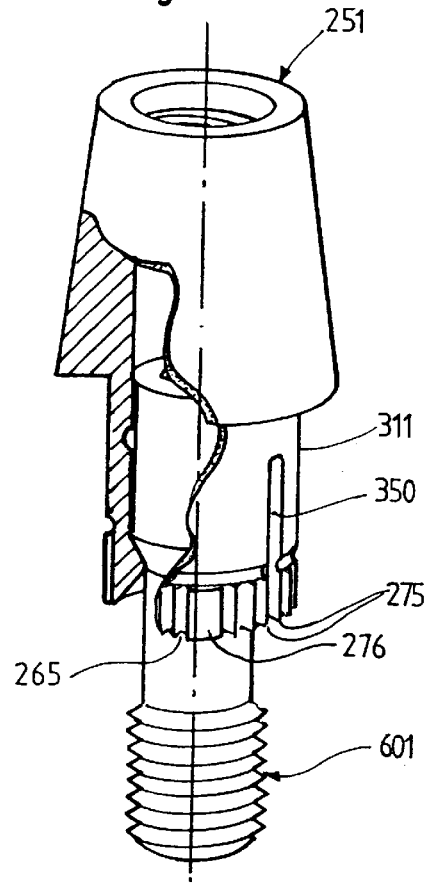
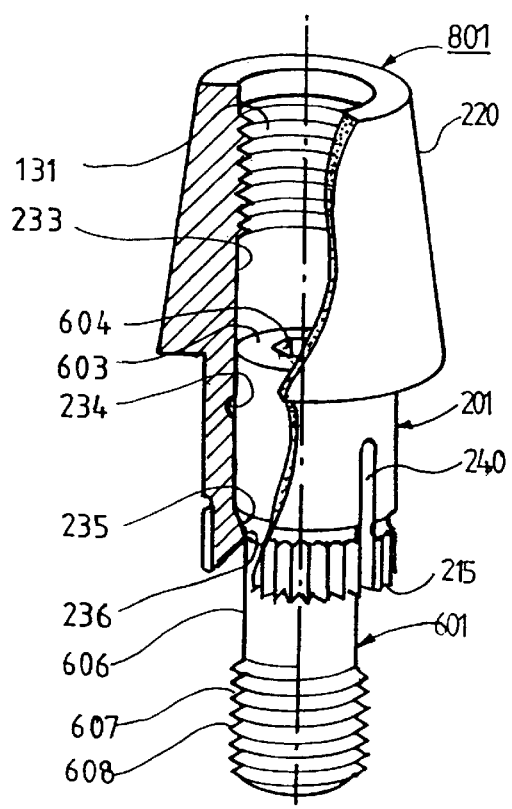
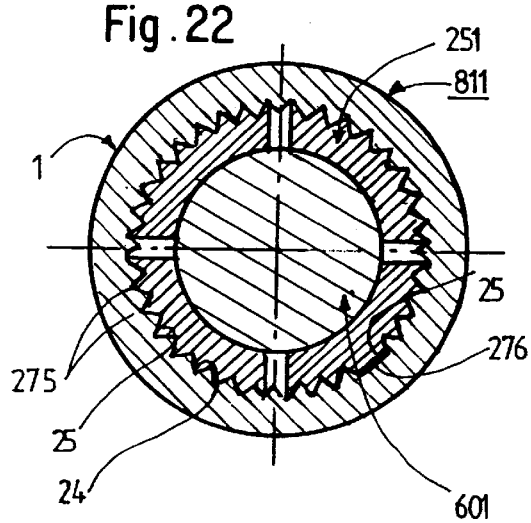

DENTAL IMPLANT AND DEVICE WITH A DENTAL IMPLANT

TECHNICAL FIELD

The invention relates to a dental implant. The implant can be used as an intraosteal implant and can be inserted into the bone of an upper or lower jaw. A secondary part can be fastened to the implant to serve for holding, and/or for the construction of, a dental prosthesis, i.e., a prosthesis with a single artificial tooth or a number of artificial teeth. The implant can furthermore serve to hold a special superstructure forming, for example, an entire single artificial tooth.

STATE OF THE ART

A device disclosed in DE 41 27 849 A has an implant and a secondary or holding part. The implant has an axial blind bore with a polygonal section. The secondary part has a polyhedral section fitting into the polyhedral section of the blind bore. The polyhedral sections are configured as dodecahedral sections, so that the secondary part can be set selectively in any one of twelve positions, i.e., can be joined non-rotationally to the implant. In many cases, however, it would be desirable if the secondary part could be joined in only a single, clearly defined position to the implant. Also, the dodecahedral mating sections provide but a relatively imprecise definition of the rotational position due to the necessary clearance. The polyhedral section of the blind bore is rather long and extends all the way to the mouth of the blind bore, so that the secondary part is never held well and accurately above the blind bore. Also, the secondary part is glued into the implant and accordingly can no longer be removed from it.

A device disclosed in EP 0 685 208 A likewise has an implant and a secondary part. The implant has an axis and a bore coaxial with it which has a tapering section and an internal thread. The secondary part can be inserted partially into the bore in the implant and has an external thread which can be driven into its internal thread. The secondary part is rotated about its axis when it is screwed into the implant, until it contacts with a tapered section the tapered section of the bore. The rotational position in relation to the axis of the secondary part which results in the assembled state depends on the production tolerances and on the torque with which the secondary part is screwed into the implant. So this implant does not permit any precise setting of the rotational position of a secondary part reaching into the bore in the implant.

DE 195 34 979 C has disclosed a device with an implant and a spacer sleeve. The implant has an axial blind bore. Its inside surface is provided with six grooves distributed about the axis of the implant. The spacer sleeve reaches into the blind bore of the implant and has lugs engaging in its grooves, so that the spacer sleeve can be set in six different rotational positions. This implant thus does not define any single, definite rotational position. Also the spacer sleeve is guided laterally only in a short cylindrical guiding portion of the bore, which has a relatively small diameter, and is supported against forces directed approximately squarely to the axis of the implant. If such forces act on a dental prosthesis held by the spacer sleeve, a long lever arm is created between the point of attack of these forces and the guiding portion of the bore, so that very great torques must be transferred from the spacer sleeve to the implant in the guiding portion of the blind bore. This, combined with the small dimensions of the guiding portion, results in a great danger that the prosthesis under stress will perform small movements—so-called micromovements—with respect to the implant, and thus a failure of the dental treatment is caused.

BRIEF DESCRIPTION OF THE INVENTION

The invention is therefore addressed to the problem of creating a dental implant which eliminates the disadvantages of the known implants, and especially makes it possible to connect to the implant a secondary and/or superstructural part, depending on its shape and intended use, in only one, clearly defined rotational position or in one which can be selected from any of several possible rotational positions.

This problem is solved according to the invention by a dental implant with an axis and a bore coaxial with this axis for fastening a secondary and/or superstructural component, wherein the bore has a positioning section with projections and interstices alternating with one another around the axis, and the dental implant is characterized in that the interstices have a plurality of first interstices of equal size and a second interstice which in at least one direction has a larger dimension than the first interstices.

The invention further relates to a device with a dental implant and with a secondary and/or superstructural part, the device according to the invention being characterized in that it has a connecting section intended to reach into the bore in the implant and to be fastened in the latter.

Advantageous embodiments of the implant and the device will appear from the dependent claims.

The first and second interstices of the dental implant according to the invention make it possible to fasten to one and the same implant secondary and/or superstructural components of optionally different configuration, which, depending on their configuration, are able to assume only a single rotational position defined by the positioning section of the implant, or which can assume a rotational position selected from several possible rotational positions, or whose rotational position is not defined by the positioning section.

The implant is preferably elongated and generally rotationally symmetrical with its axis. The bore is preferably a blind bore and has a mouth situated at one end of the implant. Each interstice of the implant is preferably straight and parallel as well as symmetrical with a plane passing through the said axis and through the middle of the groove in question. The positioning section of the implant is furthermore generally cylindrical, for example, so that the projections present between the interstices of the implant have an apex lying in a cylindrical surface coaxial with the axis. The positioning section of the implant, however, can possibly be generally conical instead of cylindrical, narrowing away from the mouth of the bore, and can have projections which separate the interstices from one another and have apexes lying in a conical surface.

The positioning section of the implant preferably defines a pitch circle, both in the case of generally cylindrical and in the case of generally conical shape, which is coaxial with the axis and conforms with the apexes of the projections of the implant. In a preferred embodiment, the second interstice is wider and/or deeper than the first interstices. The first interstices adjacent one another are at equal distances apart as measured along the pitch circle, and together they define a pitch circle division or—simply—a division. For clarification let it also be noted that the division is equal to the nth part of a full circle, n being a whole number and preferably at least 6, or better at least 10, and amounting to no more than 72, for example. The second, wider and/or deeper interstice has a dimension measured along the pitch circle that is preferably greater than one division, for example approximately or exactly equal to the sum of the dimension of a first interstice measured along the pitch circle and of one whole division or several whole divisions.

A secondary part designed to be fastened to the implant can have an inside section or connecting section, and an outside or head section. When the secondary part is fastened to the implant the inside or connecting section is situated in the bore in the implant and the outside or head section outside of the implant. The secondary parts can be configured differently according to the intended use and the medical indications. The inside or connecting section of the secondary part can have, for example, a positioning section with projections distributed along its circumference, and separated from one another by interstices. When the secondary part is fastened to the implant, the projections of the implant and of the secondary part can then engage interstices of the other part and thereby establish a rotational position of the secondary part with respect to rotations about the axis defined by the bore in the implant. In one possible embodiment of the secondary part, all projections of the secondary part have equal shapes and dimensions, so that the secondary part can be fixed in different rotational positions on the implant. The rotational position of the secondary part is thus optional and variable step by step, while each selectable rotational position is defined by the intermeshing projections and grooves of the implant and secondary part, and the angle of rotation between adjacent rotational positions is equal to the dividing angle established by the division of the equally configured (first) interstices. This method of joining a secondary part to the implant is referred to hereinafter as the multipositioning of the secondary part.

The secondary part can furthermore have a projection which in at least one direction has a greater dimension than the first interstices of the implant and is configured such that it can enter in the second interstice, but not in the first interstices of the implant. This projection of the secondary part can especially be wider than the first interstices of the implant and/or have a height that is greater than the radial depth of the first interstices of the implant. The positioning section of the secondary part then preferably has, in addition to the said projection, narrower projections for engaging the narrower first interstices of the implant, but possibly can have only just the projection engaging the second, wider and/or deeper interstice of the implant. The secondary part can then be joined to the implant only in a single rotational position as regards rotations about the axis defined by the implant. This way of joining a secondary part to the implant will be referred to hereinafter also as single positioning of the secondary part.

The secondary part, however, can also be made without a positioning section, and can be so configured that, when inserted into the bore of the implant and after it is fastened to the latter, it will not enter into the interstices of the implant. The secondary part is then continuously rotatable upon insertion into the bore in the implant, until the secondary part is fastened to the implant.

Each interstice in the implant is defined preferably at least partially by flats which are approximately or precisely parallel to a straight line passing radially to the axis through the center of the interstice in question, or form with such a straight line an angle of at most 60° and preferably no more than 45°. Furthermore, each interstice has, for example, two substantially planar lateral surfaces. The interstices can be approximately V-shaped in cross section, or they can have also a base surface and be approximately U-shaped. The interstices can furthermore be substantially completely curved, and form an arc, for example, which is no more than equal to a semicircle and, for example, smaller than a semicircle. The projection, or every projection, of the secondary part and implant engaging in an interstice has a certain free play, so that in spite of possible manufacturing inaccuracies and in spite of dimensional changes caused by temperature changes, the projection can be inserted easily into the interstice. The free play of a projection, measured tangentially to the above-mentioned pitch circle is preferably made so small that the secondary or superstructural part can be turned back and forth by no more than an angle amounting preferably to no more than 2°, or better 1°, or even no more than 0.5°.

The blind bore of the implant has preferably an internal thread serving for the removable attachment of the secondary part. If the secondary part has a positioning section with a projection or, preferably, a plurality of projections, the secondary part can be releasably fastened to the implant with an external thread which can be screwed into the internal thread of the implant. The fastening means can consist, for example, of a screw with a head urged against a surface of the secondary part, or of a headless screw which can be threaded into the secondary part. The headless screw can then have, in addition to the external thread which can be screwed into the internal thread of the implant, an external thread which can be screwed into an internal thread in the secondary part, and one of the external threads can be right-handed, for example, and the other left-handed, and/or the two external threads can have different pitches. To attach a secondary part to provide positioning, therefore, only a single additional element is needed, namely the said fastening means. If the secondary part, however, has no projection designed to engage a positioning groove in the implant, the secondary part can either also be fastened releasably to the implant, likewise with a separate fastening means of the kind described, or it may be provided with an external thread which can be screwed into the internal thread of the implant and consists, together with the remaining sections of the secondary part, of a one-piece body. Possibly a secondary part can also be provided which is fastened to the implant, not by screwing, but one which when used is first inserted releasably into the hole in the implant, and then, when it must no longer be removed, it is cemented or glued in the bore in the implant. The bore in the implant can then nevertheless have an internal thread so that the same type of implant can also be used to accommodate a threaded secondary part. If desired, however, the internal thread can be omitted from the implant. The secondary part can be joined securely and free of micromovements to the implant by the above-described screwing, cementing or gluing methods, so that in a physiological environment, it will not loosen due to micromovements.

A firm manufacturing implants according to the invention can, for example, also manufacture different variants of secondary parts to be fitted to the implants and offer one type of implant and various secondary parts to dentists and dental clinics and the like. Then, for example, a superstructure serving for the formation of a dental prosthesis can be built unreleasably on the secondary part or can be fastened releasably to the latter. Also, two or more devices each with an implant and a secondary part can serve for fastening a bridge or a dental prosthesis containing a plurality of teeth.

As already mentioned, instead of a secondary part, a special superstructural part can be fastened to an implant. Such special superstructural part can then, instead of the firm producing the implants, be custom made by a dental technician for special purposes and/or for a specific patient.

What has been described above concerning the joining of a secondary part to the implant can then apply in a substantially similar way to the attachment of a special superstructural part to an implant.

BRIEF DESCRIPTION OF THE DRAWINGS

The subject matter of the invention is explained below with the aid of embodiments represented in the drawings. In the drawings:

FIG. 1 shows an axial section taken through a part of an implant in which the bore has a positioning section in the vicinity of the bottom end of a cylindrical section, FIG. 2 an enlarged cross section taken through the implant of FIG. 1, FIG. 3 an angular elevation of the implant of FIGS. 1 as well as 2, FIG. 4 an angular elevation of an implant with a positioning section disposed as in FIG. 1, but of a different configuration, FIG. 5 an angular elevation of an implant with a positioning section arranged at its upper end, FIG. 6 an angular elevation through an implant whose positioning section is arranged below the narrower end of a tapered section of the bore, FIG. 7 an axial section taken through a straight secondary part with a positioning section arranged in the vicinity of the lower end, FIG. 8 an enlarged cross section taken along line VIII—VIII of FIG. 7 through the secondary part drawn therein and configured for multipositioning, FIG. 9 a cross section similar to FIG. 8 taken through a secondary part for single positioning, FIG. 10 an axial section taken through a bent secondary part, FIG. 11 an axial section taken through a secondary part fitting the implant of FIG. 5, FIG. 12 an axial section taken through a straight secondary part with an internal thread for fastening a stud bolt, FIG. 13 an axial section taken through a secondary part whose internal and connecting portion has a tapered external surface section, FIG. 14 an angular view of a bent secondary part with an internal thread for fastening a stud bolt, FIG. 15 an elevation of a screw, FIG. 16 an elevation of a stud bolt with two threads, FIG. 17 an elevation of another stud bolt, FIG. 18 an angular view of a secondary part according to FIGS. 7 and 8, and of a screw inserted in the latter, FIG. 19 an axial section taken through a device with an implant according to FIGS. 1 to 3 and the parts according to FIG. 18, FIG. 20 a cross section taken along line XX—XX of FIG. 19 through the device seen in the latter.

FIG. 21 an angular view of a straight secondary part according to FIG. 9 and of a screw inserted in the latter, FIG. 22 a cross section through a device with an implant according to FIGS. 1 to 3 and the parts according to FIG. 21, FIG. 23 an angular view of a device with an implant according to FIG. 4, a secondary part configured for single positioning, and a stud bolt, FIG. 24 an angular view of a bent secondary part for multipositioning, and a screw, FIG. 25 an axial section taken through a device with an implant according to FIG. 4 and parts according to FIG. 24, FIG. 26 a cross section taken along line XXVI—XXVI of FIG. 24 through the device shown therein, FIG. 27 an axial section taken through a device with an implant according to FIG. 6 and a bent secondary part according to FIG. 14, FIG. 28 an angular view of a device with an implant according to FIG. 6 and a straight secondary part, FIG. 29 an angular view of a device with an implant according to FIGS. 1 to 3 and a straight secondary part without positioning section, and FIG. 30 a cross section taken through the device according to FIG. 29.

DESCRIPTION OF PREFERRED EMBODIMENTS

Figure 5:
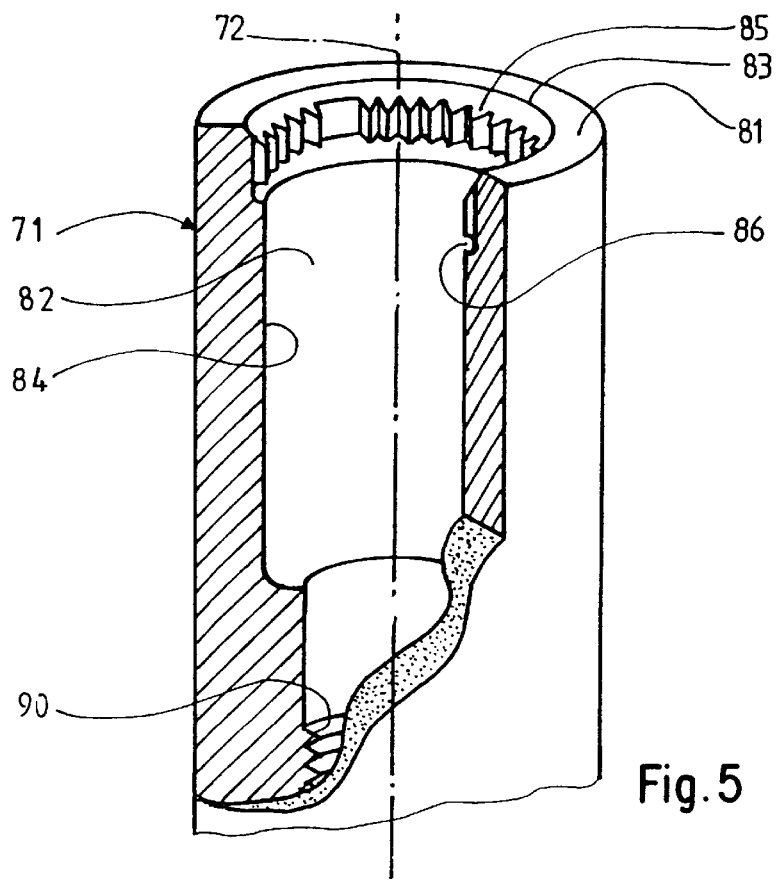

The dental implant 1 represented in FIGS. 1 to 3 is elongated as well as generally rotationally symmetrical with an axis 2 and has at the top a cylindrical, smooth circumferential surface 10. The lower part of implant 1, which is not seen in FIGS. 1 and 3, can be configured, for example, in any known or novel manner, and have, for example, a smooth cylindrical exterior or a screw thread. Also, the unseen lower part of the implant can have, for example, a cavity open at the bottom or a solid cross section at the bottom end.

The implant 1 has at the upper end an implant shoulder 11 which is formed by a planar annular surface radial to the axis 2. The implant is provided with a stepped blind bore 12 generally coaxial with the axis 2. This bore has a mouth 13 situated at the upper end of the implant and surrounded by the inner margin of the annular surface forming the shoulder 11, and downward from the latter a cylindrical main section 14, a positioning section 15, a short, generally cylindrical recess 16, a radial and/or inclined shoulder 17, a narrower cylindrical section 18, and a section 19 with an internal thread 20, in that order. The axial dimension of the positioning section 15 amounts, for example, to approximately 0.5 mm to 1 mm. The diameter of the recess 16 is equal to that of the cylindrical main section 14. The diameter of the narrower, cylindrical section 18 is at least or approximately equal to the maximum diameter of the internal thread 20. Moreover, let it be noted that the narrower cylindrical section 18 could possibly be omitted and the internal thread could directly adjoin the recess 16.

As it can be seen especially clearly in FIGS. 2 and 3, the positioning section 15 has positioning projections 23 and positioning interstices 24, 25 alternating with one another along the circumference. The positioning projections 23 are all equally configured, extend inwardly toward the axis 2 from the cylindrical surface defined by the cylindrical main section 14, taper inwardly in cross section toward their apex, and are approximately V-shaped or triangular in cross section. The positioning interstices have a plurality of equally shaped as well as equally dimensioned, especially of equal width, namely narrow, first positioning interstices 24 and a single, wider second positioning interstice 25. Each first positioning gap 23 consists of a groove or notch of approximately V-shaped cross section and has two substantially planar flanks which slope away from one another inwardly from its base toward the axis 2. The wider second positioning gap 25 has a planar or slightly curved base surface and two lateral surfaces inclined inwardly therefrom away from one another. The lateral surfaces of the gaps and the apexes of the projections are straight in axial sections and run parallel to the axis 2. The apexes of the projections 23 define a pitch circle 27 and lie on a cylindrical surface. The bases of the interstices 24, 25 together also define a cylindrical surface which coincides approximately or precisely with the cylindrical surfaces of the main section 14 and of the recess 16. The narrow first positioning interstices 24 adjacent one another are all at the same distance apart and define a division on the pitch circle 27, for example a 10° or 36-pitch division. The wider, second positioning interstice 25 is formed by the omission of one projection 23 or of two or even more projections 23 adjacent one another.

The dental implant 31 seen in FIG. 4 is very similar to implant 1, defines an axis 31 and has an implant shoulder 41, a blind bore 52 with a mouth 53, a cylindrical main section 54, a positioning section 55 and an internal thread 60. The positioning section is arranged similar to the positioning section 15 and has positioning projections 63 and positioning interstices 64, 65 following one another alternately along its circumference. The positioning projections 63 are again all of the same configuration. The positioning interstices 64, 65 have a plurality of first, narrow positioning interstices 64 and a second, wider positioning interstice 65. Each positioning projection 63 consists of a cog and has an apical surface that is arcuate in cross section. The apical surfaces of the projections form parts of a cylindrical surface coaxial with the axis of the implant 31 and they define a pitch circle. The second, wider positioning interstice 65 is formed by the omission of one positioning projection 63. Each positioning interstice 64, 65 is approximately U-shaped in cross section and/or quadrangular, and has two lateral surfaces which are planar and approximately or precisely parallel to a plane running through the axis 32 and the center of the positioning interstice in question. Also, each interstice 64, 65 has a base surface which is parallel to the axis 32 as well as arcuate or straight in cross section, and approximately coincides with the surface of the main section 54. The first, narrow positioning interstices 64 together define a division, for example a 30° or 12-pitch division.

The dental implant 71 seen in FIG. 5 has an axis 72, an implant shoulder 81 and a blind bore 82 with a mouth situated at the upper end of the implant and surrounded by the implant shoulder 81, a cylindrical main section 84, a positioning section 85 and an internal thread 90. The positioning section is situated approximately at the upper end of the implant between the mouth 83 and the cylindrical main section 84, and is separated from the latter by a recess 86. The positioning section has, for example, projections and interstices of a configuration similar to that of the positioning section 15 of implant 1, but could also be configured similar to the positioning section 55 of implant 31. The apexes of the projections of the positioning section define a cylindrical surface whose diameter is, for example, approximately or at least equal to that of the cylindrical main section 84.

Figure 6:
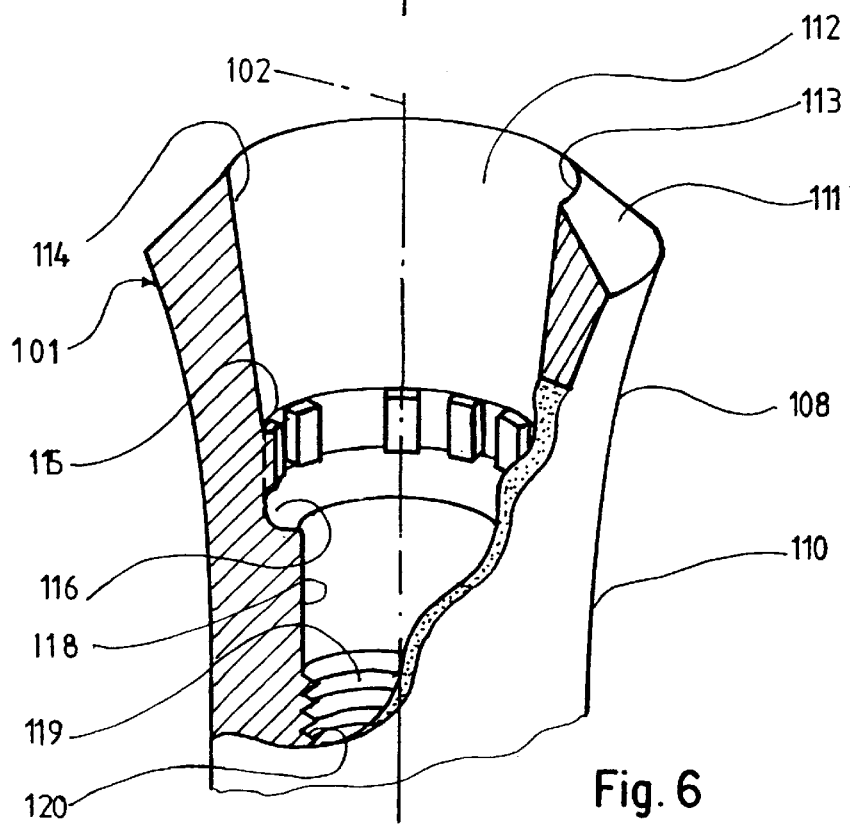

The dental implant 101 represented in FIG. 6 has an axis 102. The circumferential surface of implant 101 has at the top a flaring section 102. At the lower end thereof a cylindrical section 10 adjoins it. The implant shoulder 11 is formed by a conical, upwardly tapering annular surface. The blind bore 112 has a mouth 113 surrounded by the implant shoulder 111 and from there on down a downwardly tapering, conical main section 114, a positioning section 115, a recess 116, a cylindrical section 118 and a section 119 with an internal thread 120, in that order. The positioning section 115 is configured to be, for example, similar to positioning section 55 of implant 31, but could be configured similar to the positioning section 15 of implant 1. Let it be noted that the apexes of the positioning projections 115 define a cylindrical surface, but could possibly define a conical surface.

The secondary part 201 represented in FIGS. 7 and 8 is generally rotationally symmetrical with an axis 202 as well as straight, and has at the bottom a generally cylindrical internal and connecting section 210 intended for insertion into an implant and for releasable connection therewith. This connecting section is provided near the bottom end 212 of the secondary part with a positioning section 215. The secondary part furthermore has an outside or head section 220 tapering conically upward from the internal or connecting section and intended for arrangement outside of the implant, and it forms the upper end 221 of the secondary part. The head section 220 extends radially beyond the connecting section 210 and, when these two sections are joined, it forms a shoulder 225 with an annular, radial, planar bearing surface. The secondary part 201 is provided with an axial through-bore 230. This bore is provided near the upper end 221 of the secondary part with an internal thread 231 and has downward therefrom a shoulder 232, a cylindrical seat 233 with an annular groove 234 arranged a little below the shoulder 25, a downwardly tapering conical section 235 and a downwardly flaring, conical section 236 which extends down to the bottom end 212 of the secondary part, in that order. The two conical sections 235, 236 together form a constriction 237. A portion of the internal connection section 210 is divided by axial slits 240 from the bottom end 212 into axial, elastic, resilient tongues 241 which can be spread apart against a restoring force. For example, there are four slits and tongues, but the number and depth of the slits 240 can be varied. The slits 240 reach from the bottom end 212 to beyond the constriction, approximately to the annular groove 234 serving to improve the ability of the tongues to spread, but are not to extend all the way to the shoulder 225.

The positioning section 215 is situated in the area of the tongues 241 and has axial grooves in the outside surface of the latter which form the positioning interstices 243, between which positioning projections 245 are present. The apexes of the latter lie in the cylindrical outside surface of the inner, connecting section 210. The interstices 243 and projections 245 are, except for the gaps at the slits 240, uniformly distributed along the circumference of the secondary part. The positioning interstices 243 are all of the same shape and dimensions, have the same spacing as the positioning projections 23 of implant 1 and are at least approximately complementary to the latter. The positioning projections 245 of the secondary part 201 are likewise all of the same shape and dimensions, have the same spacing as the first positioning interstices 24 of implant 1 and are at least approximately complementary to the latter. The positioning section 215 of the secondary part 201 permits—as will later be explained—the multipositioning of the secondary part 201 with respect to the implant 1. The secondary part 251 seen in FIG. 9 has an internal connecting section 260 with a positioning section 265 configured for single positioning, and an external head section 270. The positioning section 265 has positioning interstices 273 formed by axial grooves, a plurality of first, narrow, identically shaped positioning projections 275, and a second, wider positioning projection 276. The positioning interstices 273 and the first positioning projections 275 have the same spacing as the first positioning interstices 24 of implant 1. The second, wider positioning projection 276 can clearly be formed by omitting or bridging at least one interstice of two or possibly more adjacent first positioning projections. The positioning interstices 273 of the secondary part 251 are approximately complementary to the positioning projections 23 of implant 1. Also, the first positioning projections 275 and the second positioning projection 276 of the secondary part 251 are approximately complementary to the first positioning interstices 24 or second positioning interstice 25 of implant 1.

The bent secondary part 301 seen in FIG. 10 has two axes 302, 303, forming an obtuse angle with one another, an inner connecting section 310 generally rotationally symmetrical with the axis 302 and having a positioning section 315, and a tapering outside head section 320 which is generally rotationally symmetrical with the axis 303. The shoulder 325 present between the latter and the connecting section 310 is radial as well as at right angles to the axis 302. The secondary part 301 has an angled through bore 330 which has a portion extending through the connection section 310 and the lower part of the head section 320 and coaxial with the axis 302, with a cylindrical seat 333 as well as an annular groove 334, and above the seat 333 it has a portion coaxial with the axis 303 with an internal thread 331.

The straight secondary part 351 represented in FIG. 11 has an internal or connecting section 360 with a positioning section 365, an outer or head section 370 and, at the transition between the two sections 360 and 370, a shoulder 375. The positioning section 365 is situated near the upper end of the connecting section 360 and the shoulder 375.

Figure 12:
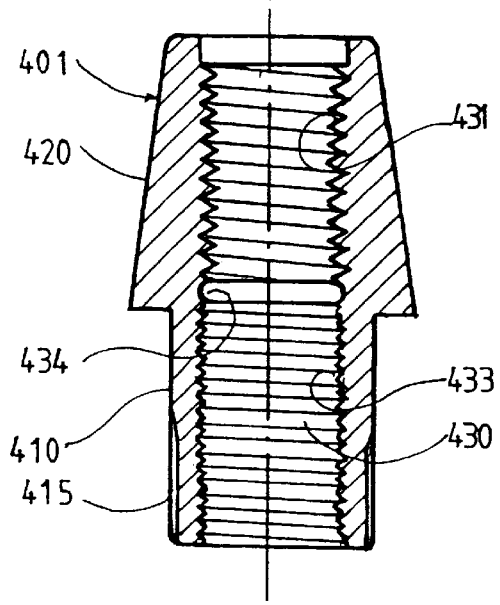

The straight secondary part 401 represented in FIG. 12 has an internal or connecting section 410 with a positioning section 415, an outer or head section 420 and an axial through-bore 430. The latter has an upper internal thread 431 near the head section 420, which serves to mount an occluding screw, a lower internal thread 433 located below the latter, substantially in the connecting section 410, and an annular groove 434 between the two threads. The connecting section in this variant is free of recesses and thus has the shape of a compact, uninterrupted ring in its cross sections through its entire length.

Figure 13:
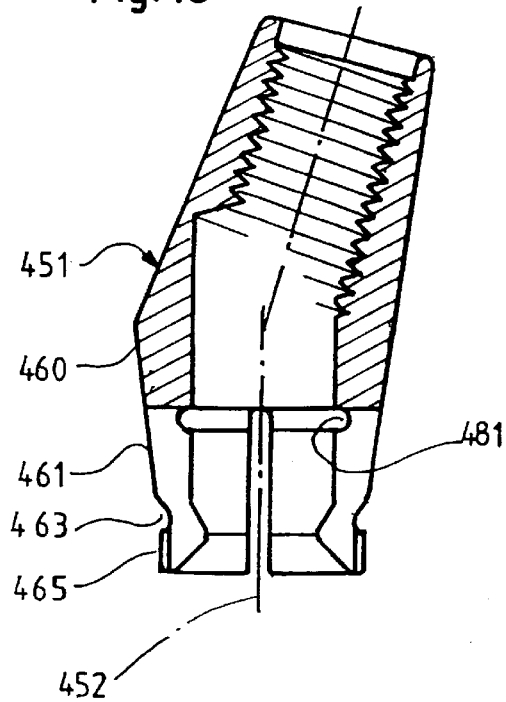

The secondary part 451 in FIG. 13 is bent at an angle and has an internal or connecting section 460 that is substantially rotationally symmetrical with its one axis 452. The latter has a conical section 461 tapering from the top down, an annular groove 463, and a positioning section 465 with a cylindrical envelope surface. The internal or connecting section 460 is configured such that its conical section 461 fits into the conical main section 114 and its positioning section 465 into the positioning section 115 in bore 112 of the implant 101 seen in FIG. 6.

Figure 14:
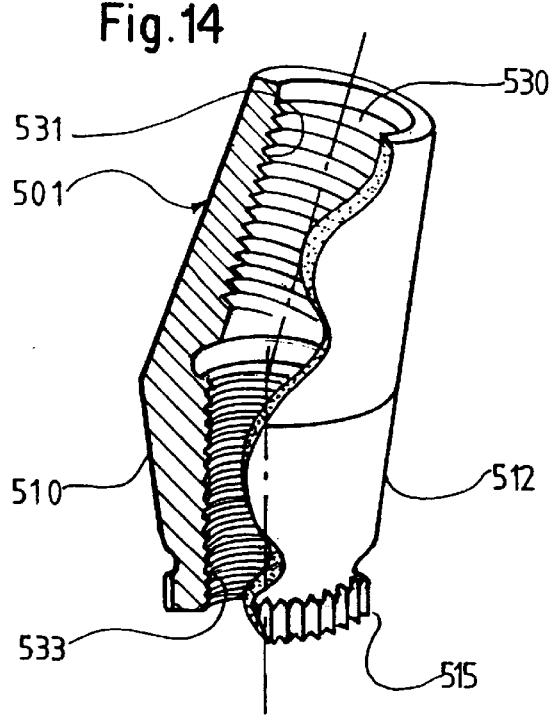

The angled secondary part 501 seen in FIG. 14 has an internal or connecting section 510, which like that of the previously described secondary part 451 has a conical section 512 and a positioning section 515. The bore 530 of the secondary part 501 is, as in the secondary part 401, provided with an upper internal thread 531 and a lower internal thread 533.

The positioning sections 315 and 415 of the secondary parts 301 and 401, respectively, shown in FIGS. 10 and 12, respectively, can be configured for multipositioning or single positioning such that they fit the implants 1 or 31. The positioning section 365 of the secondary part 351 in FIG. 11 can likewise be configured for multipositioning or single positioning, and will fit those of implant 71 in FIG. 5. The positioning section 465 of the secondary part 451 shown in FIG. 13 can also be configured for multipositioning or single positioning and will fit the implant shown in FIG. 6 or a generally similar implant whose positioning section is shaped similarly to that of implant 1. The positioning section 515 of the implant 501 shown in FIG. 14 fits an implant whose bore, like that of implant 101 in FIGS. 7 and 8, has a conical section, but has a positioning section whose profile is similar to that of implant 1 shown in FIGS. 1 to 3, but it could also be fitted entirely into implant 101. Unless otherwise described above, the implants 31, 71, 101, can be configured the same as or similar to implant 1. Also, the secondary parts 251, 301, 351, 401, 451, 501, unless otherwise described above, can be configured the same as or similar to the secondary part 201. Furthermore, each implant and secondary part consists preferably of an integral metal body.

Figure 15:
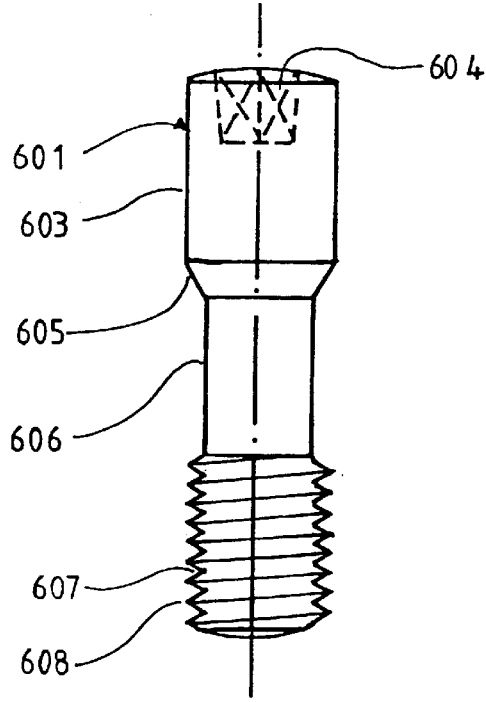

The screw 601 represented in FIG. 15 serves as fastening element for fastening one of the secondary parts 201, 251, 301, 351, 451, releasably to one of the implants 1, 31, 71, 101. The screw 601 has, in order from top to bottom, a cylindrical head 603 with a polygonal blind hole 604, e.g., a hexagonal blind hole, a downwardly tapering conical section 605, a cylindrical shaft 606, and a threaded portion 607 with an external thread 608. The cylindrical head 603 and the conical section 605 fit virtually free of radial clearance into the cylindrical seat 233 and conical section 235 of bore 230 of the secondary part 201 as well as the corresponding bore sections of the secondary parts 251, 301, 351, 451. The threaded portion 607 with the external thread 608 can be screwed into the internal thread 20 in implant 1 or one of the other implants. The diameter of the shaft 606 is, for example, equal to the core diameter of the external thread 608.

The integral bolt 701 shown in FIG. 16 serves as a fastening means for the releasable fastening of the secondary part 401 or 501 to one of the implants 1, 31, 71, 101, and has an upper external thread 703, an unthreaded cylindrical center section 704, and a bottom external thread 705. The bolt 701 is furthermore provided at the upper end with a polygonal blind hole 707, a hexagonal hole, for example. The bottom external thread 705 can be screwed into the internal thread 20 of implant 1 or other implant, and can be configured, like this internal implant thread, as a metric, right-hand standard thread. The upper external thread 703 has preferably a smaller pitch than the bottom thread, can be screwed into the bottom internal thread 433 or 533 of the secondary part 401 or 501, respectively, and consists, like the internal thread 433, 533, of a right-hand fine thread, for example. The diameter of the middle section 704 is approximately or at most equal to the core diameter of the two threads 703, 704.

The bolt 751 seen in FIG. 17 is configured similarly to bolt 701 and like the latter has an upper external thread 753 as well as a bottom external thread 755. The latter is right-handed and can be screwed into the internal thread of one of the implants, while the upper thread 753 is left-handed and has the same pitch as the bottom thread 755 or possibly a smaller pitch than the latter. The upper thread can then be screwed in a secondary part configured similar to the secondary parts 401 and 501 having a left-handed thread as their internal thread.

Figure 19:
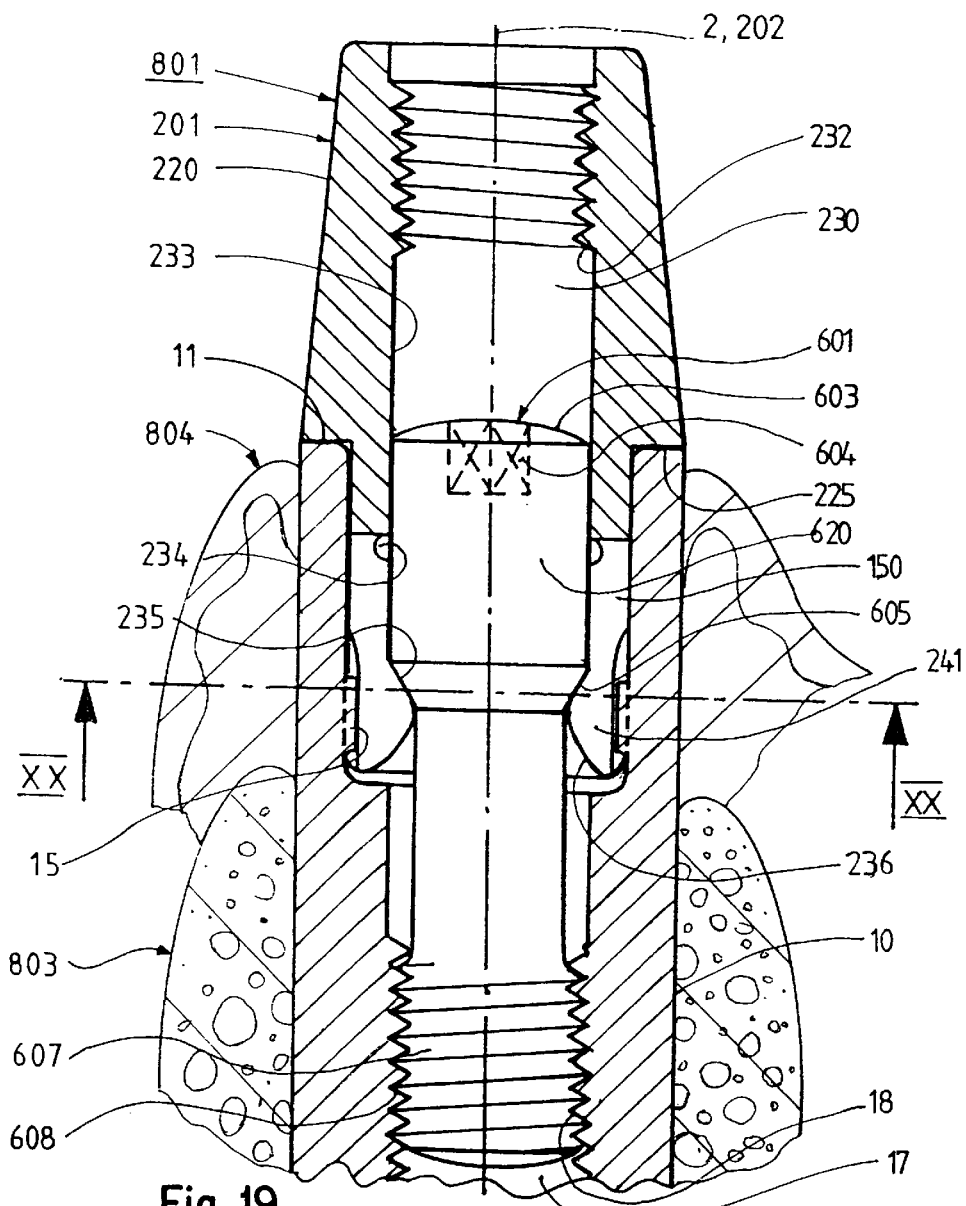
Figure 20:
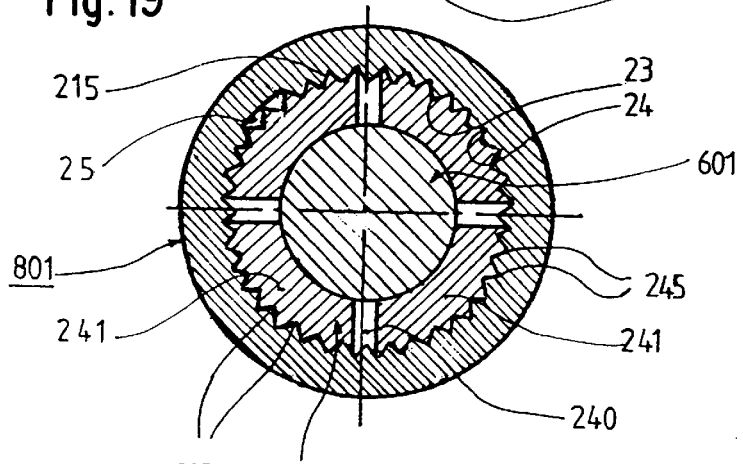

Now an explanation will be given with the aid of FIGS. 18, 19 and 20 of the use of a dental implant 1, a secondary part 201 and a screw 601 to form a device identified as a whole by 801 in FIGS. 19 and 20 for holding or forming a dental prosthesis. In FIG. 19, a jaw bone 803 of the lower jaw of a patient and the gum tissue 804, i.e., the gingiva, covering the jaw bone, are indicated. The implant 1 is anchored in a bore in the jaw bone 803 such that the implant shoulder 11 protrudes from the latter.

Before the secondary part 201 is joined to the implant 1, the head 603 of screw 601 has preferably already been introduced from below, with a momentary spreading of the tongues 241, into the bore 230 of the secondary part 201 by the manufacturer of the various parts of the device 801, so that the head 603 and the beveled section 605 enter into the cylindrical seat 233 in which they are rotatable and axially adjustable to a limited degree between the shoulder 232 and the beveled section 235. The secondary part 201 then holds the screw 601, as represented in FIG. 18. The screw 601 and the secondary part 201 are then inserted together axially into the blind bore 12 of the implant 1. The cylindrical main section 14 of bore 12 of the implant then centers the connecting section 210 of the secondary part on the axis 2. When the screw is introduced into the implant and reaches the start of the internal thread 20 of the implant, its head is momentarily set back in bore 230 of the secondary part. The secondary part 201 can then be rotated on its axis 202, and the axis 2 of implant 1 coinciding therewith, such that the secondary part 201 arrives at the desired position—i.e., rotational position—with respect to implant 1. The secondary part is then inserted more deeply into the implant until the shoulder 225 of the secondary part contacts the implant shoulder 11. Thus, most of the positioning projections 245 of the positioning section 215 of secondary part 201 enter into one of the first positioning interstices 24 of the positioning section 15 of the implant. Also, depending on the width of the second positioning interstice 25 of the implant, two or more positioning projections 245 of the secondary part enter into the second positioning interstice 25, unless perchance one of the slits 240 is there. Anyway, positioning projections 23 engage positioning interstices 24 of the secondary part. The intermeshing positioning projections and interstices of the implant and secondary part secure the latter against rotation and define its orientation. Since all the positioning projections 245 of the secondary part 201 are of the same configuration, the latter accepts multipositioning and it can be positioned selectively in any of 36 possible, precisely defined rotational positions corresponding to the ten-degree or 36-point division of the first, narrow positioning interstices 24 of the implant. After the secondary part is positioned the screw 601 can be driven into the internal thread of the implant by means of a tool introduced from above into the bore 230 of the secondary part and into the polygonal blind hole in the screw, until the beveled section 605 of the screw is (again) in contact with the conical section 235 of the hole in the secondary part, drives the secondary part downward, spreads the tongues 241 and thereby additionally clamps the secondary part to the implant. The conical peripheral or external surface of the external or head section 220 of the secondary part 201 then seamlessly merges with the cylindrical surface 10 of the implant at the outer margins of the joined shoulders 225 and 11 of the secondary part and implant, respectively.

FIGS. 21 and 22 illustrate the formation of a device 811 with an implant 1, a straight secondary part 251 formed as in FIG. 11 for single positioning and a screw 601. The secondary part seen in FIG. 21 contains the screw 601 and can be inserted together with the latter into the implant 1 represented in FIG. 22, which previously has been anchored in a jaw bone, not shown. When the secondary part 251 is joined to the implant, the second, wider positioning projection 276 of the positioning section 265 of the secondary part 251 can engage the second, wider positioning interstice 25 of the implant. The first, narrow positioning projections 275 of the secondary part can then be engaged in first, narrow positioning interstices 24 of the implant 1. The secondary part 251 can therefore be fastened in only one position, i.e., rotational position, on the implant 1.

Figure 23:
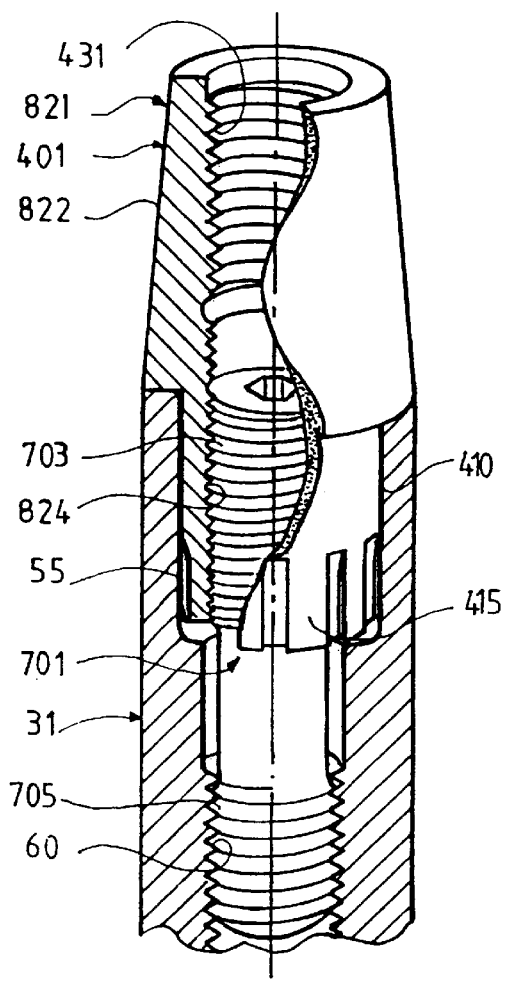

The device 821 seen in FIG. 23 has an implant 31 and a straight secondary part 401 which has a positioning section configured for single positioning and fitting the positioning section 55 of implant 31, with a plurality of first, narrow positioning projections and a second, wider positioning projection 415. To assemble the device 821, the external thread 703 of bolt 701 is screwed, for example, so far into the lower internal thread 433 of secondary part 401, that the bolt 701 stops at least approximately at the bottom end of the upper internal thread 431. The bolt and the secondary part joined thereto can then be introduced together into the implant fastened in a jaw bone, so that the positioning section of the secondary part comes into engagement with the positioning section 55 of the implant as well as fastens it non-rotatably to the implant, while the bolt is still situated above the internal thread 60 of the implant. Thereafter the bolt can be rotated with a tool engaging its hexagonal socket so as to drive the lower external thread 705 of the bolt into the internal thread 60 of implant 31. The upper external thread 703 of the bolt which previously had been screwed into the secondary part is thus also driven downward, but remains in the internal thread 824 of the secondary part.

Figure 24:
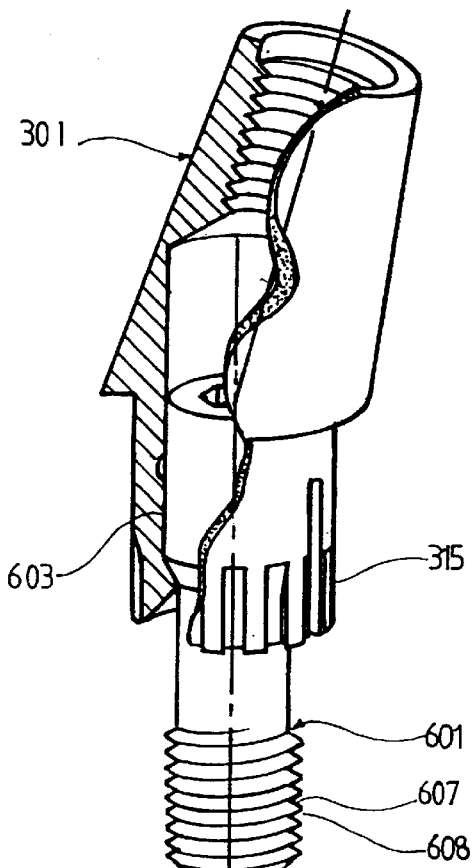
Figure 25:
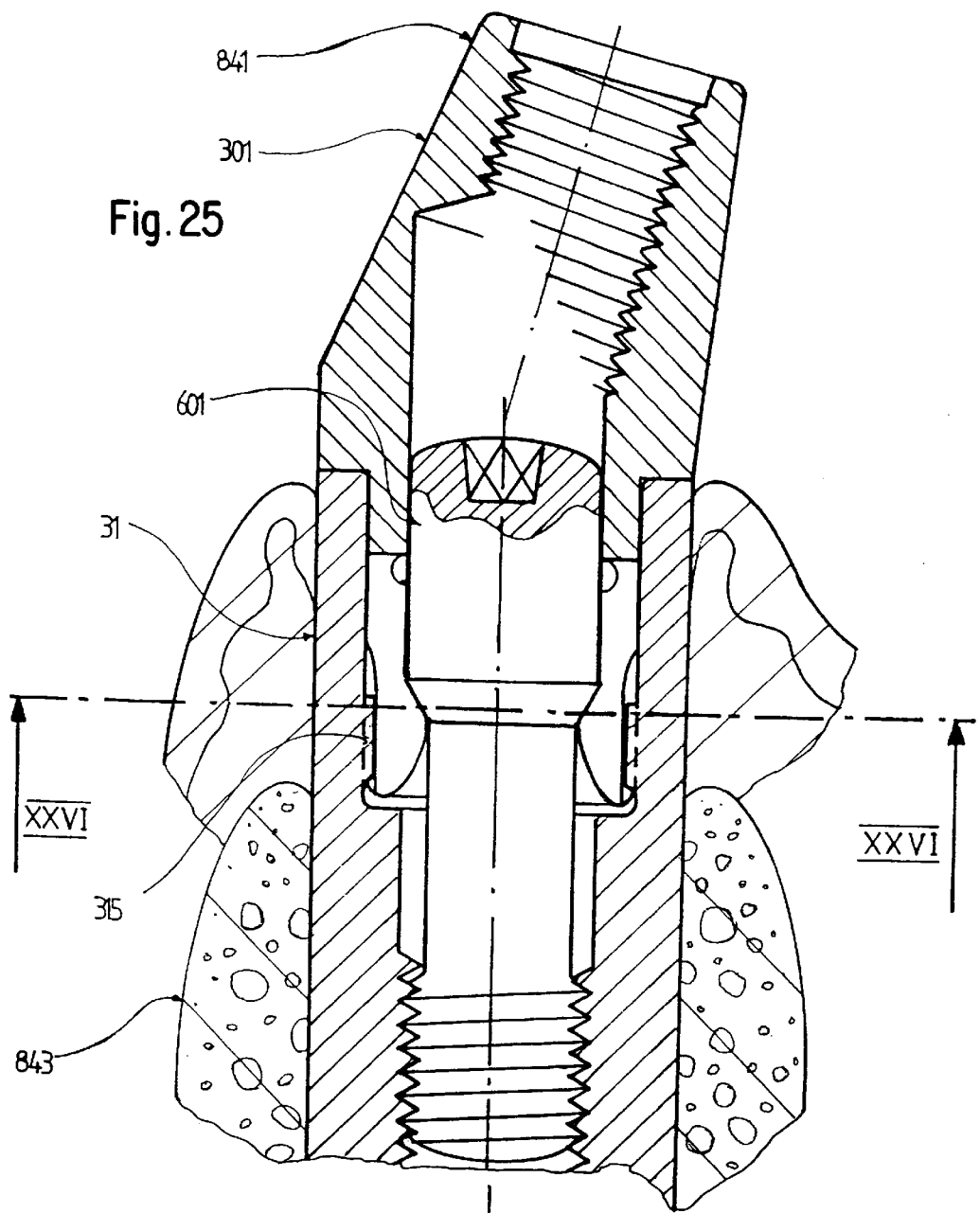
Figure 26:
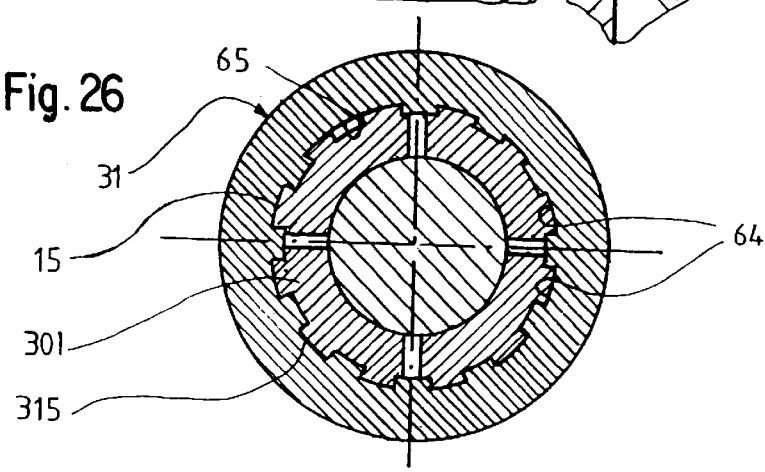

The device 841 represented in FIGS. 24, 25, 26, has an implant 31 inserted into a jaw bone 843, a bent secondary part 301 and a screw 601. The positioning section 315 of the secondary part is configured to fit the implant 31 and for multipositioning, and accordingly it has only positioning projections which are all equally wide.

Figure 27:
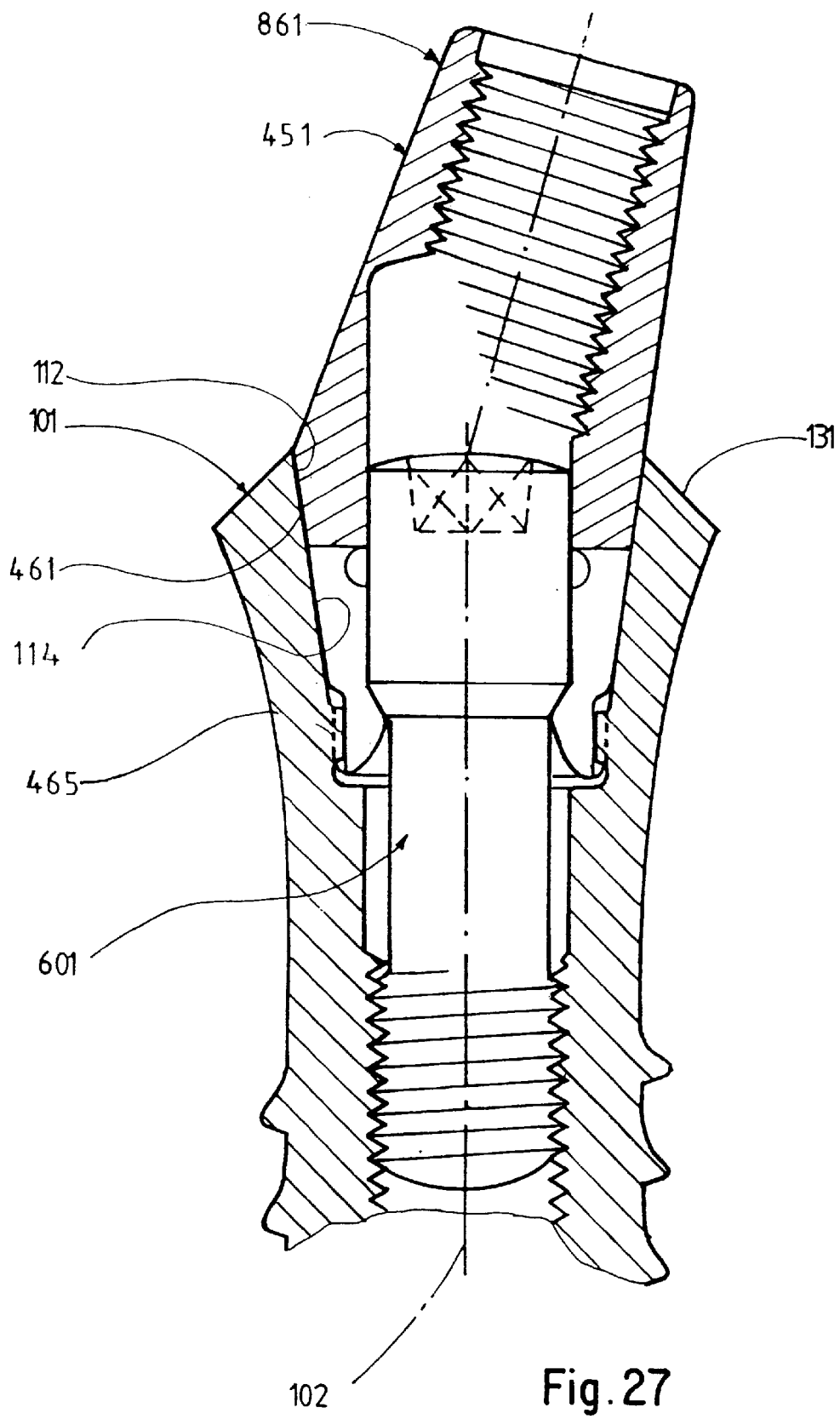

The device 861 seen in FIG. 27 has an implant 101, a bent secondary part 451 and a screw 601. The conical section 461 of the secondary part 451 is seated in the conical main section 114 of the blind bore 112 of implant 101. The conical main section 114 centers the secondary part on the axis 102 and simultaneously forms an abutment which establishes the axial position of the secondary part. The secondary part 451 is positioned by positioning section 465 in a rotational position in the implant and is fastened releasably to the implant by the screw 601.

Figure 28:
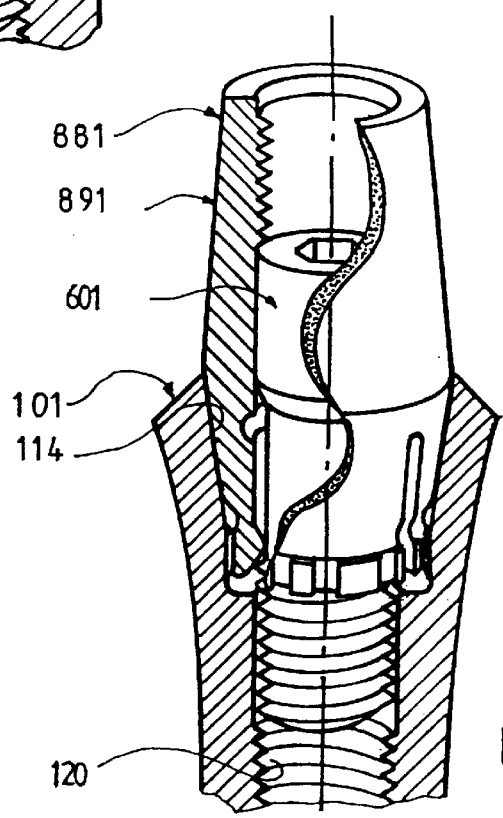

The device 881 represented in FIG. 28 has an implant 101, a screw 601, and a secondary part 891. The latter is in part similar to the secondary part 451 represented in FIG. 13, but is configured straight and for a single positioning in the implant 101. The device 881 is shown in FIG. 28 in a state wherein the screw 601 is not yet screwed into the internal thread 120 of the implant, but the secondary part is already positioned.

Figure 29:
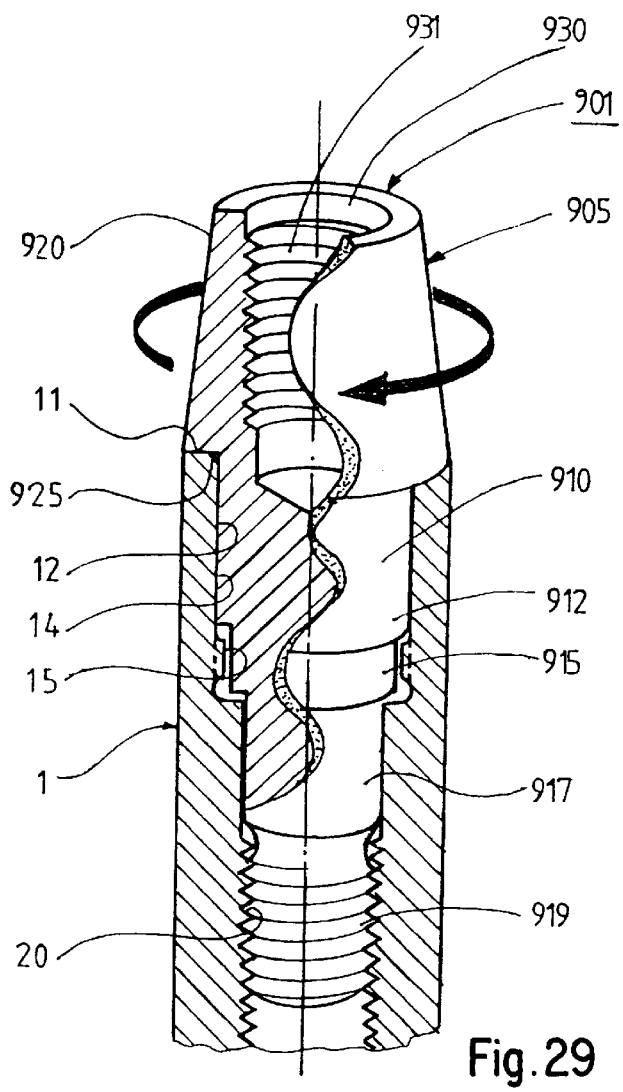
Figure 30:
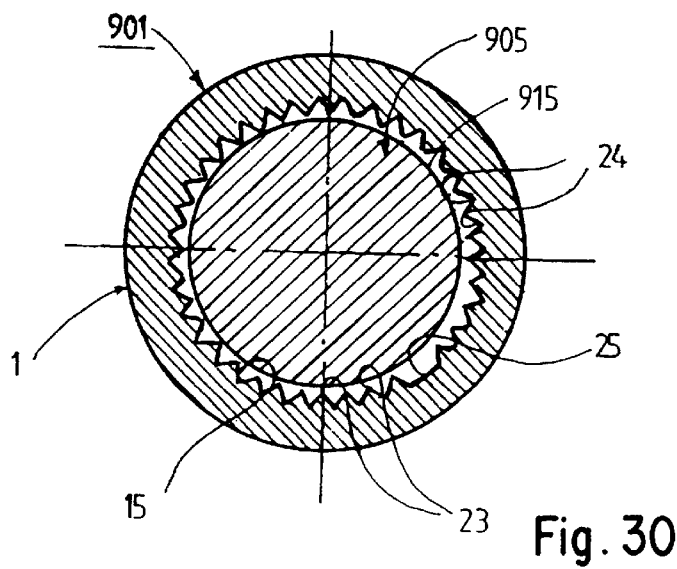

The device 901 represented in FIGS. 29 and 30 has an implant 1 and a one-piece secondary part 905 with an internal, connecting section 910. The latter has, in order from top down, three cylindrical sections 912, 915, 917, which become thinner in steps, and an external thread 919. The cylindrical section 912 is seated with little or no radial clearance in the cylindrical main section 14 of the blind bore 12 of the implant. The cylindrical section 915 is near the level of the positioning section 15 of the implant and has a diameter that is no more than equal to the diameter of the cylinder defined by the apexes of the positioning projections of the implant and preferably less than this diameter. The external thread 919 is screwed into the internal thread 20 of the implant. The secondary part 905 has furthermore an external, head section 920, a shoulder 915 and an axial blind bore 930 with an internal thread 931. The secondary part thus has no section entering into the positioning section 15 of the implant and to screw the secondary part's external thread 919 into the internal thread 20 of the implant it can be rotated around the axis of the implant until the shoulder 925 of the secondary part lies on the implant shoulder 11 and the secondary part is tightly joined to the implant. The device 901 can be used, for example, whenever the implant is used in the interforaminal area of the lower jaw.

Unless otherwise stated above, the devices described in connection with FIGS. 21 to 30 are assembled like the device shown in FIGS. 18 to 20 and have properties similar thereto.

Also, features of different implants described can combined with one another and, for example, in the case of implant 101 shown in FIG. 6, the positioning section can be arranged in a manner similar to the implant 71 shown in FIG. 5, at the upper end of the blind bore 112 or in the middle of the length of the conical main section of the blind bore. Likewise, features of different secondary parts described can be combined with one another. For example, a secondary part can also be made for the implant 101 of FIG. 6 which, like the secondary part 905 seen in FIGS. 29 and 30, can be screwed into the implant 101 without positioning. Also, the described implants, secondary parts and fastening means can be combined as well as fastened together in other ways to form devices or connecting arrangements.

Furthermore, a secondary part or special superstructure can be fastened to the implant, which has an internal, connecting section situated in the blind bore and is not screwed into the blind bore of the implant but is cemented or glued into this blind bore and even, for example, in its internal thread. The secondary part or superstructural part can also have a pillar-like outside section which does not lie on the implant shoulder. Also, a crown or the like can be fastened, say by cementing and/or gluing, to the pillar-like outside section. This crown can then lie with a bearing surface on the implant shoulder in a gap-free manner and have an outside surface which adjoins in gap-free, step-less and to some extent smooth as well as steady manner the circumferential and/or outside surface of the implant.

What is claimed is:

1. Dental implant with an axis (2, 32, 72, 108) and a bore (12, 52, 82, 112) coaxial therewith for fastening a secondary part and/or superstructural part (201, 251, 301, 351, 401, 451, 905), the bore (12, 52, 82, 112) having a positioning section (15, 55, 85, 115) with projections (23, 63) and interstices (24, 25, 64, 65) alternating with one another about the axis (2, 32, 72, 208), characterized in that the interstices (24, 25, 64, 65) have a plurality of first, equally dimensioned interstices (24, 64) and a second interstice (25, 65) which in at least one direction has a greater dimension that the first interstices (24, 64).

2. Implant according to claim 1, characterized in that the second interstice (25, 65) has a greater width and/or a greater depth than the first interstices (24, 64), the width being tangential to a circle (27) coaxial with the axis (2, 32, 72, 108) and conforming to the positioning section (15, 55, 85, 115).

3. Implant according to claim 2, characterized in that the first interstices (24,64) define a graduation on the circle and the second interstice (25, 65) has a dimension measured along the circle (27) which is equal to the sum of a dimension of a first interstice (24, 64) measured along the pitch circle and of a whole division or of several whole divisions.

4. Implant according to claim 1, characterized in that the projections (23, 63) have apexes, that the latter define a cylindrical surface conforming with the latter, that each interstice (24, 25, 64, 65) is defined at least in part by surface sections which are straight lines running approximately parallel to a the axis (2, 32, 72, 102) through the center of the interstice or form with such a straight line an angle of no more than 60° and preferably of no more than 45°, each interstice (24, 25, 64, 65) having preferably two substantially planar lateral surfaces parallel to the axis (2, 32, 72, 102).

5. Implant according to claim 1, characterized in that the bore (12, 52, 82, 112) has a mouth (113, 53, 83, 113) and an internal thread (20, 60, 90, 120) for the releasable fastening of the secondary part and/or superstructural part (201, 251, 301, 351, 401, 451, 501, 891) and that the positioning section (15, 55, 85, 115) is disposed between the mouth (13, 83, 113) and the internal thread (20, 60, 90, 120) of the bore (12, 52, 82, 112), the bore (12, 52, 82, 112) having for example also a cylindrical or conical main section (14, 54, 84, 114) for centering the secondary part and/or superstructural part (201, 251, 301, 351, 401, 451, 501, 891), and the main section (14, 54, 84, 114) being disposed, for example, between the positioning section (15, 55, 115) and the mouth (13, 113) or between the positioning section (85) and the internal thread (90).

6. Device with a dental implant (1, 31, 71, 101) according to claim 1, and with a secondary and/or superstructural part (201,251,301, 401, 451, 501, 891, 905), characterized in that the latter has a connecting section (210, 260, 310, 360, 410, 460, 910) intended to extend into the bore (12, 52, 82, 112) of the implant (1, 31, 71, 101) and to be fastened therein.

7. Device according to claim 6, characterized in that the secondary and/or superstructural part (201, 251, 301, 401, 41, 501, 822, 891) has at least one projection (245, 275, 276) for engagement in an interstice (24, 25, 64, 65) of the implant (1, 31, 71, 101) and is thus positionable in at least one rotational position with respect to the axis (2, 32, 72, 102) and securable against rotation about the latter, that a separate fastening element is present for the releasable fastening of the secondary and/or superstructural part (201, 251, 301, 401, 451, 501, 891) to the implant (1, 31, 71, 101), and that the fastening element has an external thread (608, 705, 755) which can be screwed into an internal thread (20, 60, 90, 120) of the bore (12, 52, 82, 112), the fastening element being formed, for example, by a screw (601) with a head (603) or by a bolt (701, 751) with an external thread (703, 753) which can be screwed into an internal thread (433, 824) of the secondary and/or superstructural part (401, 822).

8. Device according to claim 7, characterized in that the secondary and/or superstructural part (201, 301) has a plurality of projections (215) which are all of the same dimensions and are distributed such that the secondary and/or superstructural part (201, 301) can be positioned with respect to the axis (2, 32, 72, 102) in various rotational positions of the implant (1, 31, 71, 101).

9. Device according to claim 7, characterized in that the secondary and/or superstructural part (251) has a projection (276) which is of such configuration and dimensions that it can engage in the second interstice (25, 65), but not in any of the first interstices (24, 64) of the implant (1, 31, 71, 101), so that the secondary and/or superstructural part (251) is positionable with respect to the axis (2, 32, 72, 102) only in one single rotational position of the implant (1, 31, 1, 101), the secondary and/or superstructural part (251) having for example at least one other projection (275) which, when the secondary and/or superstructural part (25) is fastened to the implant, engages a first interstice (24, 64) of the implant (1, 31, 71, 101).

10. Device according to claim 7, characterized in that the secondary and/or superstructural part (201, 251, 301, 351, 451, 891) has an end (212), a bore (230, 330) opening into the latter, with a constriction (237), and slits (240) which divide a section of the secondary and/or superstructural part (201, 251, 301, 351, 401, 451, 501, 891), which forms the said end (212) and the constriction (237), into resilient tongues (241) which can be spread apart from one another, and that the fastening element has a portion which can be introduced by the said end (212) of the secondary and/or superstructural part (201, 251, 301, 351, 401, 451, 501, 891), with a momentary spreading of the tongues (241), into the bore (230, 330) of the secondary and/or superstructural part (201, 251, 301, 351, 401, 451, 501, 891) and then can be displaced axially to a limited extent and rotatably held in the latter, and when the secondary and/or superstructural part (201, 251, 301, 351, 401, 451, 501, 891) is fastened to the implant it lies against the constriction (237).

11. Device according to claim 6, characterized in that the secondary and/or superstructural part (905) is configured such that, in the state in which it is fastened to the implant, it does not engage in its interstices (24, 25, 64, 65).

* * * * *